United States Patent [19]

Milnamow

[11] 4,144,887

[45] * Mar. 20, 1979

[54] DIAPER WITH TAB FASTENER HAVING BACKING WEB AND FACE WEB

[75] Inventor: John P. Milnamow, North Barrington, Ill.

[73] Assignee: Johnson & Johnson, New Brunswick, N.J.

[*] Notice: The portion of the term of this patent subsequent to Oct. 26, 1993, has been disclaimed.

[21] Appl. No.: 734,205

[22] Filed: Oct. 20, 1976

Related U.S. Application Data

[63] Continuation-in-part of Ser. No. 617,902, Sep. 29, 1975, Pat. No. 3,987,793.

[51] Int. Cl.² ............................................. A61F 13/16
[52] U.S. Cl. ..................................... 128/287; 128/284
[58] Field of Search ................... 128/284, 287, 290 R; 428/41; 24/DIG. 11, 67, 73 VA

[56] References Cited

U.S. PATENT DOCUMENTS

| | | | |
|---|---|---|---|
| 3,610,244 | 10/1971 | Jones, Sr. .................... | 128/287 |
| 3,616,114 | 10/1971 | Hamaguchi et al. ............ | 128/284 X |
| 3,833,456 | 9/1974 | Reed et al. .................... | 128/287 |
| 3,893,460 | 7/1975 | Karami ........................ | 128/287 |
| 3,987,793 | 10/1976 | Milnamow ..................... | 128/287 |
| 4,020,842 | 5/1977 | Richmond et al. ............... | 128/287 |

*Primary Examiner*—John D. Yasko

[57] ABSTRACT

A disposable diaper having a facing sheet defining a diaper inside surface for direction toward an infant and a backing sheet defining a diaper outside surface is provided with adhesive tabs comprising a backing web and a face web. The backing web is folded over to form first and second anchoring legs which are attached to a marginal portion of the diaper received therebetween. The face web has a fixed end permanently attached to the second anchoring leg, and a free working portion provided with a layer of adhesive. The free working portion is movable from a folded-over storage position, in which the adhesive layer is releasably attached to a release region provided on the outer surface of the first anchoring leg, to a working position in which the adhesive layer is available to secure the diaper about an infant. If desired, the backing and facing webs may comprise an integral elongated tape segment. Secondary fastening means may be provided for refastening the diaper about an infant. In addition, an adhesive-free region may be provided at the distal end of the face web to facilitate the gripping of the free working portion.

10 Claims, 7 Drawing Figures

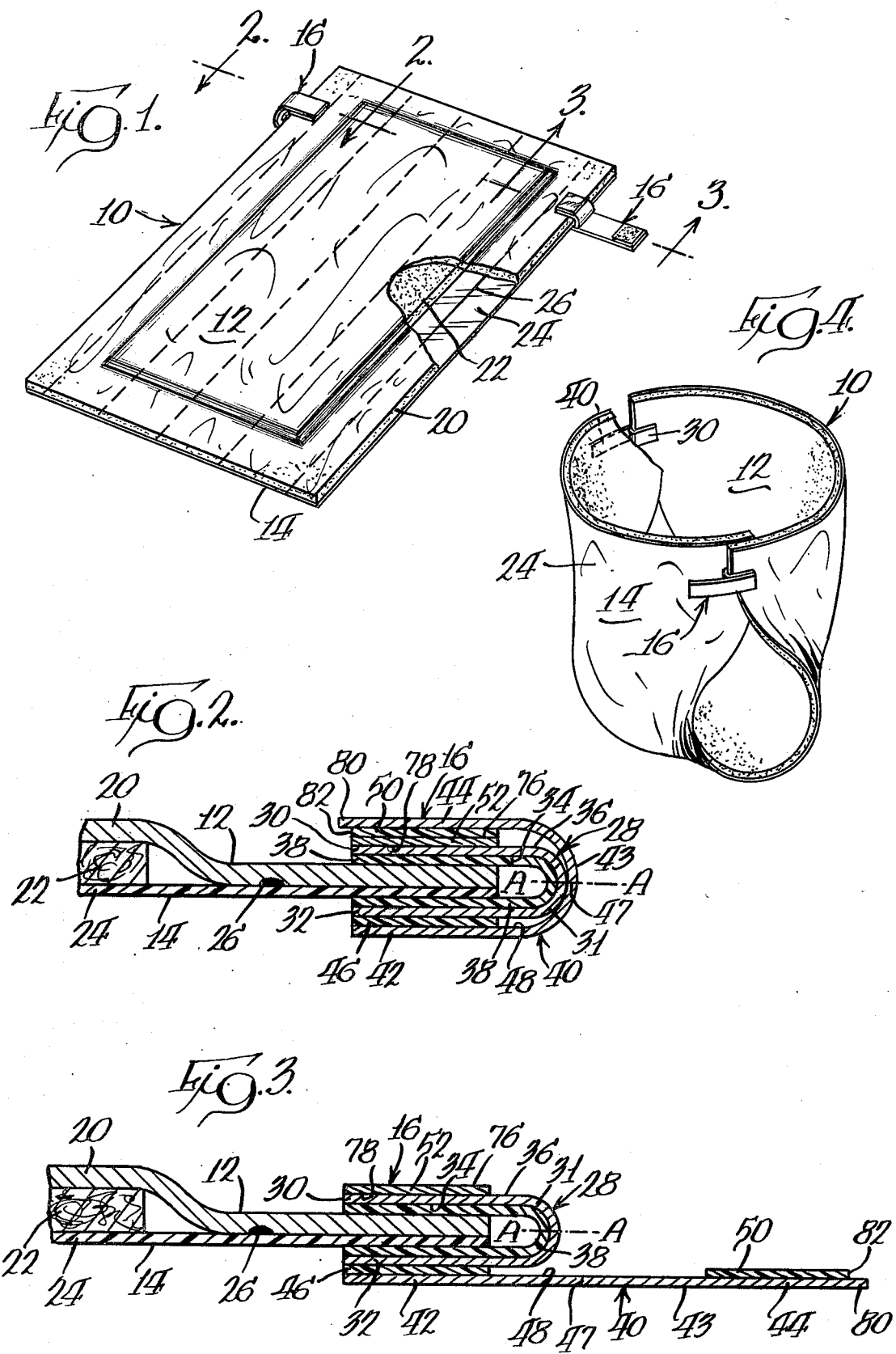

DIAPER WITH TAB FASTENER HAVING BACKING WEB AND FACE WEB

CROSS-REFERENCE TO RELATED APPLICATIONS

This application is a continuation-in-part of my co-pending application Ser. No. 617,902, filed on Sept. 29, 1975 and now U.S. Pat. No. 3,987,793.

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moister-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two specially interconnected tape portions. Moreover, the turned up end of the reinforcing tape portion causes the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two co-extensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially co-extensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper, but has the disadvantage in that each tape fastener is comprised of two or more separate tape segments which are joined together so as to produce a common area of joinder for both fastener anchoring legs and the fastener securing portion and thereby adding complexities and expense to the manufacturing process, as well as requiring careful positioning during diaper manufacture.

SUMMARY OF THE INVENTION

According to the present invention, tape tabs are used on each side of a diaper to secure the diaper about an infant. Each tab is provided with an adhesive-free tab gripping means and includes a backing web which is folded over to define two anchoring legs permanently attached to a marginal portion of the diaper received therebetween and a face web connected to one anchoring leg and having a free working portion provided with a layer of adhesive. The free working portion is movable from a folded-over storage position, in which the adhesive layer is releasably attached to a release region provided on the outer surface of the other anchoring leg to a working position in which the adhesive layer is available to secure the diaper about an infant.

In one embodiment, the backing web may comprise an integral extension of the face web, in which case the tab is a unitary elongated tape segment. In another embodiment the backing web is a separate elongated tape segment, and the face web has a fixed end which is permanently attached to the outer face of one of the anchoring legs by means of an adhesive layer which can be separate from the layer of adhesive on the free working portion which can be a continuation thereof.

The tab gripping means in each case is an adhesive-free region, unitary with the free working portion, which protrudes inwardly from and beyond the edge of the release means when the free working portion is in a storage position to provide a convenient, graspable appendage for separating the adhesive-coated free working portion from the release means.

The release means may comprise a release coating printed or otherwise deposited on a portion of the face of the anchoring leg which faces in the same direction as the diaper inside surface, or a release strip having a release coating on one face thereof and an adhesive coating on the opposite face by means of which the release strip is adhered to the anchoring leg. Other suitable means for releasably adhering the free working portion of the tab to the diaper can also be employed.

The tape tab fasteners of the present invention remain flat against the diaper when in the folded configuration and will not interfere with the diaper manufacturing machinery and the subsequent folding and packaging operations. Additional features of this invention include the utilization of a tape tab which is relatively easy to affix to the diaper, and which provides good bond strength and permanent attachment of the tab to both the diaper facing sheet and backing sheet. In the embodiment, where a separate adhesive layer is used to attach the fixed end of the face web to the backing web, i.e., those embodiments having an uncoated central region of the face web, the tab can be torn or severed in the central region to facilitate removal of the tab from an infant. The uncoated central region also provides more elasticity in the central region of the face web to absorb and dissipate stresses which are imposed on the tab as the infant moves about, thereby minimizing the load on the free working portion of the face web.

BRIEF DESCRIPTION OF THE DRAWINGS

FIG. 1 is a perspective view, partially broken away to show interior detail, of an open unfolded diaper in accordance with one of the embodiments of the invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3;

FIG. 4 is a perspective view of the diaper of FIG. 1 in a configuration assumed by the diaper when placed about an infant;

DESCRIPTION OF THE PREFERRED EMBODIMENTS

Figure 5:
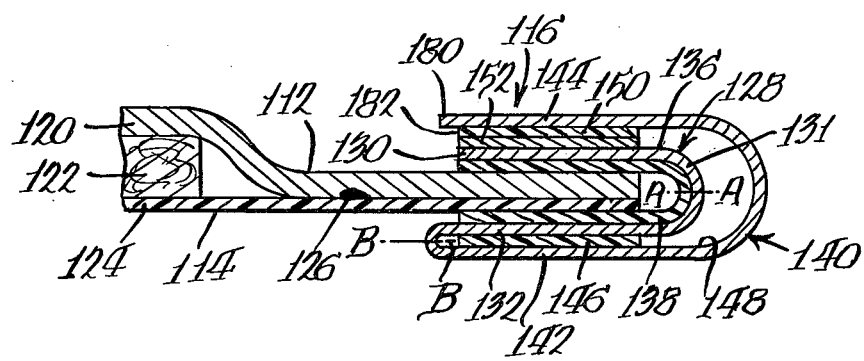
FIG. 5 is a fragmentary cross-sectional view, similar to FIG. 2, and illustrating an alternate embodiment of the invention.

In the following description, two digit numerals are used to refer to the embodiment illustrated in FIGS. 1-4, three digit numerals in the one hundred series are used to refer to the embodiment illustrated in FIG. 5, and three digit numerals in the two hundred series are used to refer to the embodiment illustrated in FIGS. 6 and 7. The same last two digits in each numeral designate similar elements in the various embodiments.

Disposable diaper 10, illustrated in FIGS. 1 and 4, is of substantially quadrilateral configuration and presents inside surface 12 for direction toward an infant and outside surface 14 for direction away from the infant. Adhesive tab fastener means such as tab 16 are attached to diaper 10 for securing diaper 10 about an infant. As described in greater detail below, tab 16 is movable from a folded-over storage position illustrated in FIG. 2 to a working position which is illustrated in FIG. 3.

Referring to FIGS. 1-3, diaper 10 comprises moisture-pervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than the backing sheet 24 and is centrally disposed thereon; however, absorbent pad 22 can be made coextensive with backing sheet 24, if desired. Facing sheet 20 is juxtaposed and preferably substantially coextensive with backing sheet 24. Both the facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2 and 3, adhesive tab 16 comprises a backing web 28 which is folded over about fold line A—A situated at or near the marginal edge of diaper 10 so as to define first and second anchoring legs 30, 32 each having an inner face 34 and an outer face 36, and central section 31. Anchoring legs 30, 32 preferably are about equal in width and length, and are in a substantially juxtaposed relationship to one another. Anchoring legs 30, 32 receive a marginal portion of the diaper therebetween, and are provided with an adhesive coating which may comprise a continuous adhesive coating 38 on the inner face 34 thereof. First anchoring leg 30 is permanently attached to facing sheet 20 and second anchoring leg 32 is permanently attached to backing sheet 24 by means of adhesive coating 38 which is substantially coextensive with both anchoring legs 30 and 32. Adhesive coating 38 can be a pressure-sensitive adhesive composition, a heat-activated or solvent-activated adhesive composition, or the like.

Tab 16 further includes face web 40 zone-coated with an adhesive and having fixed end 42, central region 43 and free working portion 44. Fixed end 42 of face web 40 is permanently attached to second anchoring leg 32 by means of adhesive coating 46 which may be provided on either the inside face 48 of fixed end 42, the outer face 36 of second anchoring leg 32 or on both. Pressure-sensitive adhesive coating 50 is provided on inside face 48 of free working portion 44, faces in the same direction as diaper inside surface 12 when tab 16 is in the working position, and provides a securement means which can be moved from the closed, storage position of FIG. 2 to the open working position of FIG. 3 for fastening the diaper about an infant. Uncoated central region 43 permits tearing or severing of the tab fastener once the diaper has been placed about the infant. If desired, line of weakening 47 can be provided in uncoated central region 43 of face web 40 to facilitate tearing of the tab fastener upon removal of the diaper from the infant. Since central region 43 of face web 40 is uncoated, central region 43 has greater elasticity than the end portions and has the capacity to absorb and dissipate stress imposed on face web 40.

Release means 52 is provided and is adapted to be releasably attached to adhesive coating 50. The release means may be provided only on outer face 36 of first anchoring leg 30 to provide a release region facing substantially in the same direction as diaper inside surface 12. When tab 16 is in the storage position of FIG. 2, adhesive coating 50 on free working portion 44 of face web 40 is releasably adhered to release means 52 which is substantially coextensive with adhesive coating 50. Projecting portion 80 provides convenient gripping means for free working portion 44.

Release means such as region 52 in FIGS. 2 and 3 may comprise a ribbon segment or release strip carried by backing web 28 and provided with a release coated face 76 which provides the release region, and an adhesive coating on opposite face 78 by means of which the release strip is anchored to backing web 28. Release coated face 76 faces in the same direction as diaper inside surface 12 and is substantially coextensive with adhesive coating 50 on free end 44 of face web 40 when tab 16 is folded to the storage position. Alternatively, release means 52 may comprise a release coating, such as a silicone release compound, or the like, on the outer face 36 of backing web 28 and which is substantially coextensive with adhesive coating 50 on free working portion 44 of face web 40 when tab 16 is folded to the storage position.

It is desirable to provide a gripping means to facilitate grasping tab 16 to separate adhesive coating 50 on free working portion 44 of face web 40 from release means 52 preparatory to fastening the diaper about an infant.

As shown in FIG. 2, free working portion 44 includes projecting portion 80 which extends inwardly of diaper 10 beyond outermost margin or end 82 of adhesive coating 50. Segment 80 provides a gripping means for separating adhesive coating 50 on face web 40 from release means 52.

In the embodiment illustrated in FIG. 5, backing web segment 128 comprises an integral extension of face web segment 140 so that tab 116 is a unitary elongated tape ribbon folded about fold line B—B which delineates face web segment portion 140 from backing web segment portion 128. Backing web segment portion 128 is folded about fold line A—A to define first and second anchoring legs 130, 132 and central portion 131. Adhesive coating 146 may be provided along a portion of inside face 148 of face web portion 140 or outer face 136 of second anchoring leg 132 to adhesively attach backing web segment portion 128 to face web portion 140. Alternatively, the part of face web segment portion 140 which is contiguous with anchoring leg 132 can be secured thereto by heat sealing when thermoplastic web materials are utilized.

The relative positions of anchoring legs 130 and 132 in FIG. 5 can also be reversed so that fold line B—B is situated on the facing side of the diaper. In such a case, a line of weakening is provided along fold line B—B, projecting lift tab portion 180 is omitted, and release coating 152 is carried by anchoring leg 132 rather than by anchoring leg 130 as shown in FIG. 5. The line of weakening along fold line B—B is severed after the tab fastener has been attached to the usual marginal location on the diaper either as a subsequent step during diaper manufacture or when preparing to position the diaper about an infant. After severance, the tab fastener is substantially the same as that shown in FIG. 3; however, a manufacturing expedient is obtained inasmuch as the entire tab fastener can be initially manufactured from a single tape ribbon.

Figure 6:
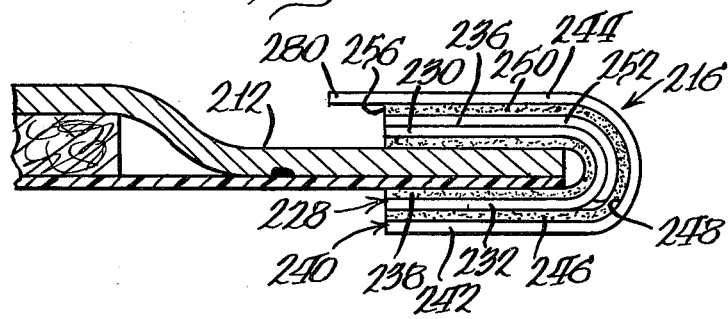
FIG. 6 is a fragmentary cross-sectional view similar to FIG. 2 and illustrating an alternate embodiment of the invention in a folded-over storage position.
Figure 7:
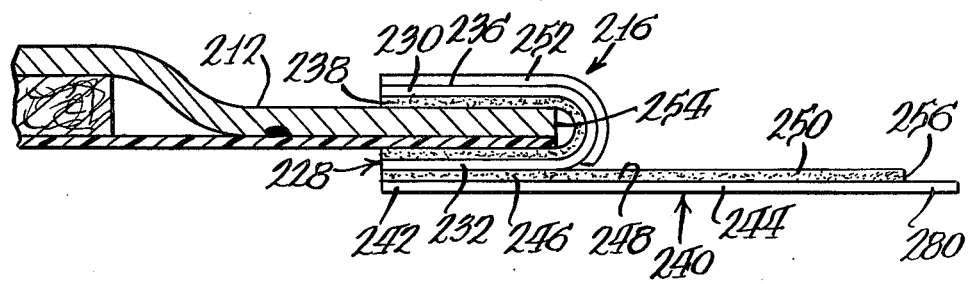
FIG. 7 is a fragmentary cross-sectional view of the same embodiment as in FIG. 6 but showing the tab in an extended working position.

In the embodiment illustrated in FIGS. 6 and 7, tab 216 includes backing web 228 which has release means 252 provided on outer face 236 of first anchoring leg 230, and face web 240 which has fixed end 242, a grippable adhesive-free region 280 at the opposite end of the face web, and free working portion 244 situated between the fixed end 242 and adhesive-free region 280. Fixed end 242 is permanently attached to second anchoring leg 232 by means of adhesive coating 246 which may be provided on either the inside face 248 of fixed end 242, the outer face 236 of second anchoring leg 232, or on both. Pressure-sensitive adhesive coating or layer 250 is provided on inside face 248 of free working portion 244, faces in the same direction as diaper inside surface 212 when tab 215 is in the working position, and provides a securement means which can be moved from the closed, storage position of FIG. 6 to the open working position of FIG. 7 for fastening the diaper about an infant. In the storage position, adhesive coating 250 on free working portion 244 of face web 240 is releasably adhered to release means 252 which is substantially coextensive with adhesive coating 250. Backing web 228 is provided with adhesive layer 238 for securement to the diaper.

As shown in FIG. 6, tab 216 includes adhesive-free region 280 which protrudes inwardly away from lateral margin 254 of diaper 210 and beyond outermost margin or end 256 of adhesive coating 250. To be easily grippable, adhesive-free region 280 preferably is at least about ⅛ inch in length, preferably is at least about ⅛ of the length of free working portion 244, and also projects inwardly beyond edge 256 of release means 252 when tab 216 is in the folded-over storage position. The adhesive-free region 280 thereby provides a convenient gripping means for separating adhesive coating 250 on free working portion 244 from release means 252 so that free working portion 244 can be moved to the extended working position shown in FIG. 7 in which adhesive coating 250 is available for use in securing the diaper about an infant.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 50 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd$^2$.

In addition, facing sheet 20 can be formed of a nonapertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001" thick. Another suitable material for this purpose is a polyethylene terephthalate web having a thickness of about 0.005". Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custon fit. The adhesive fasteners are then prepared for use by pulling free working portion 44 of face web 40 away from its temporary engagement with release means 52, exposing adhesive coating 50 which was releasably adhered to release means 52 and separable therefrom. The tabs are then used to secure the diaper in the desired position by simply urging the pressure-sensitive adhesive surfaces in contact with the adjacent outer surface of the diaper. The applied diaper assumes the configuration illustrated in FIG. 4.

The foregoing description and the drawing are illustrative but are not to be taken as limiting. Still other variations and modifications are possible without departing from the spirit and scope of the present invention.

What is claimed is:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:

a backing web folded over to form first and second anchoring legs each having an inner face and an outer face, said web extending around and receiving a marginal portion of the diaper therebetween, and said inner face of said anchoring legs being provided with an adhesive coating by means of which said anchoring legs are permanently attached to the diaper marginal portion;

a face web having a fixed end permanently attached to said second leg, a grippable adhesive-free region at the opposite end of said face web, and a free working portion situated between said fixed end and said adhesive-free region, said free working portion being provided with a layer of pressure-sensitive adhesive on one face thereof; and release means releasably attached to said adhesive layer on said free working portion;

said grippable adhesive-free region extending inwardly away from said lateral margin of the diaper and beyond said release means and said first leg of said backing web, and said free working portion being separable from said release means to make said free working portion available for use in securing said diaper about an infant.

2. The disposable diaper as defined in claim 1 wherein said release means is carried on said outer face of said first anchoring leg and provides a release region facing in the same direction as said diaper inside surface;

said free working portion being movable from a folded-over storage position wherein said free working portion is releasably adhered to said release region to a working position wherein said free working portion of said face web is available for use in securing said diaper about an infant.

3. The disposable diaper as defined in claim 2 wherein said release region is substantially coextensive with said layer of pressure-sensitive adhesive on said free working portion.

4. The disposable diaper as defined in claim 2 wherein said layer of adhesive on said free working portion faces in the same direction as said diaper inside surface when said tab fastener means is extended to said working position.

5. The disposable diaper as defined in claim 2 wherein said release means is a release coating on said outer face of said first anchoring leg.

6. The disposable diaper as defined in claim 5 wherein said release coating comprises a silicone release compound.

7. The disposable diaper as defined in claim 2 wherein said release means comprises a ribbon segment which has one face adhesively affixed to the outer face of said first anchoring leg and an opposite face having a release coating.

8. The disposable diaper as defined in claim 1 wherein said face web is adhesively attached to said backing web.

9. The disposable diaper as defined in claim 2 wherein said grippable adhesive-free region extends for a distance which is at least about ⅛ of the length of said free working portion and projects inwardly from and beyond said release region when said free working portion is in the storage position.

10. The disposable diaper as defined in claim 1 wherein said face web further includes a second adhesive-free region between said fixed end and said free working portion.

* * * * *